United States Patent [19]
Schirmer

[11] 4,015,898
[45] Apr. 5, 1977

[54] UPRIGHT WIDE ANGLE STEREO OPHTHALMOSCOPE

[76] Inventor: Kurt Ernest Schirmer, 56 Granville Road, Hampstead, Quebec, Canada

[22] Filed: Apr. 14, 1975

[21] Appl. No.: 567,850

[52] U.S. Cl. .................................. 351/6; 350/145; 351/16
[51] Int. Cl.² .......................................... A61B 3/12
[58] Field of Search ............. 351/6, 7, 16; 350/145, 350/146

[56] References Cited

UNITED STATES PATENTS

| 3,475,082 | 10/1969 | Strietzel | 351/6 |
| 3,664,730 | 5/1972 | Cardona | 351/6 |

OTHER PUBLICATIONS

K. E. Schirmer, "The Upright . . . Ophthalmology" *Archives of Ophthalmology*, Jan. 1967, pp. 67–70, vol. 77.

Primary Examiner—Paul A. Sacher
Attorney, Agent, or Firm—Alan Swabey & Co.

[57] ABSTRACT

An ophthalmoscope-microscope having an object lens at one end of a housing and an inverting, reversing and separating prism provided in the housing in the optical axis of the object lens, a binocular viewer attached to the housing and being aligned with the optical axis of the object lens in the prism and including in one embodiment mirrors at 45° to the optical axis for deflecting the bundles of rays to the left and right eyes of an observer for upright unreversed stereoptical imagery of the retina of a patient's eye. The stereoscope viewer can be replaced by a stereo microscope viewer comprising separate objective lens for left and right bundles of rays, Porro prisms for uprighting and reversing the rays from the objective lens, and eyepieces for angularly magnifying the image passing to the left and right eyes of an observer for upright stereo viewing.

9 Claims, 3 Drawing Figures

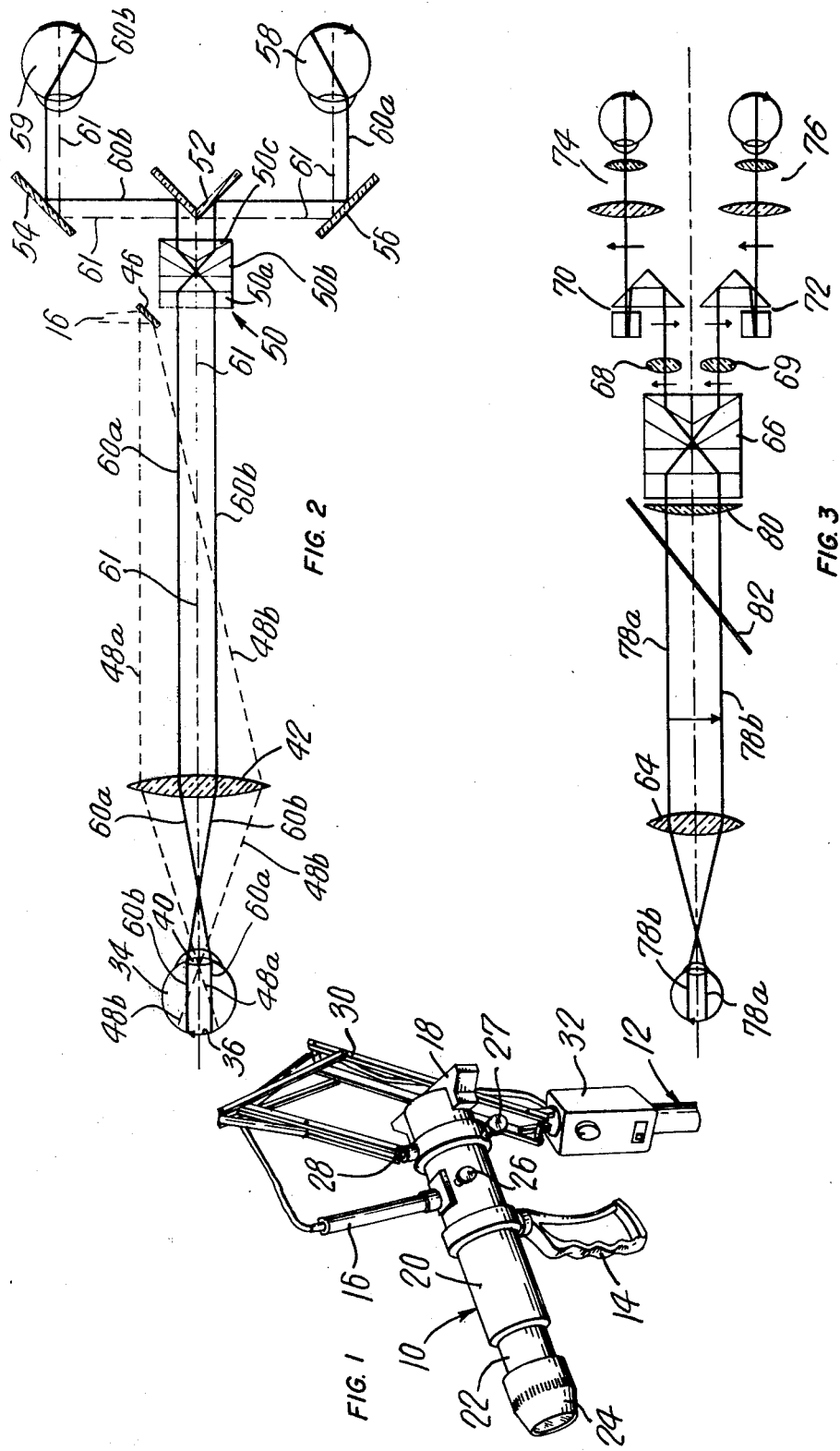

UPRIGHT WIDE ANGLE STEREO OPHTHALMOSCOPE

BACKGROUND OF THE INVENTION

1. Field of the Invention

The present invention relates to an instrument for examining the fundus of the eye, and more particularly to an improved stereo ophthalmoscope or microscope for examining the fundus of the eye and for presenting an upright and unreversed image of the retina to the observer.

2. Description of the Prior Art

When the fundus of the eye is subject to examination and ophthalmic surgery, it is of advantage that the magnified image be as faithful as possible to the object. In the past, with indirect ophthalmoscopy, the fundus was viewed as an inverted reversed image since conventional optical systems were used.

Attempts have been made to provide upright and unreversed imagery in fundus ophthalmoscopes. One such ophthalmoscope includes a single objective lens, a separating prism spaced from the object lens separating the image rays into two groups and passing the rays to separate reflecting and laterally correcting prisms and then through an erecting lens system for each eye. This ophthalmoscope achieves the desired result, but the accuracy at which prisms and lenses must be placed in the housing and the overall length thereof makes it less practical.

SUMMARY OF THE INVENTION

It is an aim of the present invention to provide a simple stereo ophthalmoscope which provides an upright unreversed image to the observer. The simplicity of the ophthalmoscope reduces the cost thereby making stereo upright ophthalmoscopes available to students and experienced ophthalmoscopists alike.

It is also an aim of the present invention to provide an ophthalmoscope with a wide angle view greater than with presently known upright ophthalmoscopes.

A construction in accordance with the present invention comprises an ophthalmoscope having a housing and an optic lens at one end of the housing for passing a bundle of rays from the fundus of an eye, a single inversion roof top prism in the housing optically aligned with the object lens, said prism including means for inverting, reversing and separating the rays passing therethrough, binocular means for passing the rays emitting from said prism to the left eye and to the right eye through respective eyepieces, said binocular means having a common axis with the object lens and the rays passing through the left and right eyepiece providing a stereo upright unreversed image of the retina to the observer.

In a more specific construction in accordance with the present invention, there is an elongated housing having a object lens at one end thereof for passing a bundle of rays from the fundus of an eye, a single inversion roof top prism in the housing spaced a distance from the object lens coinciding with the optical axis of the object lens, said prism having means for inverting, reversing and separating said bundle of rays, binocular means in said housing including a right eyepiece and a left eyepiece, said binocular means having a common axis with the optical axis of the object lens, and means for passing the separated bundles of rays emitting from the prism to each eyepiece.

In a more specific embodiment of the invention, the binocular means includes a reflecting means extending at 45° on either side of the optical axis at the exit of said prism and a pair of reflecting means for passing the rays being separated to each eyepiece.

In a further embodiment, the binocular means includes a pair of object lenses on the exit side of the prism for passing the separated bundles of rays, and erecting-reversing prisms are provided in each binocular body for psssing the bundle of rays to each eyepiece.

The optical system is included within a housing so that the image appears projected for the viewer in the direction of the object. The elements of the inversion system are fixed relative to the optical axis thereby permitting no image shift.

The inversion means comprises and Uppendahl prism, or other inversion prism for inverting the aerial image formed by the objective lens. The inversion prism inverts the image forming rays and crosses them to the opposite side of the prism to provide an unreversed image to the observer.

BRIEF DESCRIPTION OF THE DRAWINGS

The invention will now be described in detail having reference to the accompanying drawings, in which:

FIG. 1 is a perspective view of the ophthalmoscope of one embodiment of the invention;

FIG 2 is a longitudinal horizontal cross-section taken through the opthalmoscope of FIG. 1; and FIG. 3. is a schematic arrangement of the ophthalmoscope with a microscopic binocular attachment.

DESCRIPTION OF THE PREFERRED EMBODIMENT

Referring now to FIG. 1, there is shown an ophthalmoscope 10 on a stand 12. The ophthalmoscope 10 has a piston grip 14 for directing the tube 20. A binocular viewer 18 is provided at one end of the tube 20, while an external light source 16 is mounted to the tube 20.

A telescoping tube 22 slides within the tube 20 and is adjustable therewith. The telescopic tube 22 mounts an object lens housing 24.

The stand 12 includes a spring-biased elbow arm 30 on an upright 32, and it is connected to the tube 20 by means of a universal joint 28.

Referring now to FIG. 2 of the drawings, an emmetropic eye is schematically shown at 34, which includes a fundus area 36 encompassing the retina 38. The eye 34 also includes eye lens 40.

The ophthalmoscope 10 includes an object lens 42 facing the eye 34. Rays emitted from the eye, passing through the anterior focal point of the eye lens 40 and the nodal point of the eye 40, form parallel bundles that are formed into an inverted image by the objective lens 42. The bundle of rays passing through the anterior focal point are shown parallel to the optical axis and are represented schematically by the lines 60a and 60b.

The Uppendahl prism 50 includes a triangular prism section 50a, a quadrangular section 50b, and a roof section 50c. The Uppendahl prism 50 is directly aligned along the optic axis 61. The binocular viewer 18 includes a right angle mirror 52 aligned such that the apex of the right angle mirror is in the optical axis 61 and each reflecting surface of the mirror is at 45° to the optic axis 61. The viewer also includes mirrors 54 and 56 respectively mounted on each side of the mirror 52 which is adapted to deflect the incident rays at right angles to respectively the left and right eyes of the observer through observing windows 55 and 57.

The light source 16 which penetrates within the tube 20 projects a light beam to a mirror 46 which in turn deflects the light beams to the object lens 42 which in turn converges the light beams through the eye lens 40 and onto the fundus 36. The illumination could be provided by a flexible fiber-optics member or by a self-contained light source.

In operation, the ophthalmoscope 10 is located such that the optical axis of the ophthalmoscope is aligned with the pupil of the eye to be observed. The observer places himself behind the binocular viewer 18 such that his left eye 58 and right eye 59 are aligned with the apertures 57 and 55 respectively of the binocular viewer 18.

The light 16 is turned on, and an illumination beam from the light 16 is deflected by the mirror 46 towards the object lens 42. The mirror 46 is placed above or to the side of the sight path of the instrument so that it does not interfere therewith. The light beams 48a and 48b pass through the lens 42 and are converged to pass through the eye lens 40 to illuminate the fundus 36. Once the fundus 36 is illuminated by the beams 48a and 48b, the retinal image represented by an upright arrow will be projected as a bundle of image rays 60a and 60b through the eye lens 40 and the object lens 42. The projected image from the retina is inverted and reversed.

In the present specification, the terms "upright" and "inverted" will be used in reference to the vertical axis of the image while the terms "reversed" and "unreversed" will refer to the lateral or horizontal axis of the image.

An aerial image is formed which is inverted and reversed. The parallel retinal image rays 60a and 60b as well as those rays along the optical axis 61 pass into the Uppendahl prism 50. The retinal image rays 60a and 60b are passed to the Uppendahl prism 50 in the form of bundles. These bundles of rays are twisted through 180° as they pass through the three sections 50a, 50b and 50c of the Uppendahl prism and exit with the bundle of rays 60b on the side of the right eye 59 and the bundle of rays 60a on the left side of the optical axis 61.

The right angle mirror 52 reflects the bundle of rays 60b and 60a towards mirrors 54 and 56 respectively which in turn deflects the upright unreversed bundle of rays towards the respective eyes 59 and 58. As the bundle of rays 60b passes through the eye lens of the eye 59, they pass through the nodal point of the eye 59 and inverted and the retinal image is projected on the retina of the eye 59 in an inverted position. However, as is well known, in order that the brain register the image in an upright position, it must be inverted on the retina of the observer. Similarly, the bundle of rays 60a is passed to the retina of the eye 58. Accordingly, upright unreversed stereopsis is obtained from the use of the ophthalmoscope 10.

Referring now to FIG. 3, there is shown schematically another embodiment of the present invention in which a microscopic binocular system is used. The structure of this embodiment includes an object lens 64 which would be mounted in a tube similar to that described with reference to FIGS. 1 and 2. Similarly, an Uppendahl prism 66 is shown for correcting the inverted and reversed image projected by the lens 64 and for separating the bundle of rays. At the exit side of the Uppendahl prism 66, there is provided a binocular viewer including object lenses 68 and 69 directing the bundles of rays to Porro prisms 70 and 72 respectively. Finally, an eyepiece 74 and 76 is provided corresponding to the right and left eyes of the observer. This added microscope device with its objective lens 68 is focused onto the aerial image in the tube behind the objective lens 64. The initially magnified aerial image within the front tube is further magnified by the objective lens 68 of the added low power microscope. After this double linear magnification, the second aerial image is angularily magnified by the ocular lenses 74a and 74b of the eyepiece 74, for instance, projecting into the observer's eye a reversed image which gives the observer the impression of upright imagery.

The binocular means represented in FIG. 3 must be arranged such that the optical axis of the object lenses 68 and 69 form an Isosceles triangle and intersect at the plane of the aerial image formed in the tube between the object lens and the Uppendahl prism 66. An adjustment could be provided to adjust the binocular bodies such that the angle of the optical axis of the object lenses 68 and 69 can be adjusted.

A field lens 80 could also be used, and it is shown located directly in front of the prism 66. When using the field lens 80, the object lens 64 must be fixed at a predetermined distance from the field lens 80, and, therefore, the tube cannot be adjustable in the longitudinal direction. However, the two stereoptical images presented to the observer give the impression that the observer is looking at the retina from within the patient's eye. The use of a field lens 80 is not necessary, but would be used in a more sophisticated microscope.

A pellicle 82 may also be used to reflect the illumination beams from a light source. The pellicle is a semi-transparent plastic thin sheeting with a light silver coating and does not appear to reflect dirt particles as does a conventional semi-transparent mirror.

It is also noted that the binocular viewer 18 and the magnifying or microscopic binocular system illustrated in FIG. 3 can be interchanged merely by releasably attaching the binocular units to the tube 20.

I claim:

1. An ophthalmoscope having an elongate linear housing and an objective lens at one end of the housing for passing a bundle of rays from the fundus of an eye, a single inversion roof top prism in the housing optically aligned with the objective lens, said prism including means for inverting, reversing and separating the rays passing therethrough, binocular means connected to the housing for passing the rays emitting from said prism to the left eye and to the right eye through respective eyepieces, said binocular means having a common axis with the objective lens and the rays passing through the left and right eyepiece providing a stereo upright unreversed image of the retina to the observer.

2. An ophthalmoscope as defined in claim 1, wherein said prism is an Uppendahl prism.

3. An ophthalmoscope as defined in claim 2, wherein a pair of deflecting mirrors are provided in the binocular, along the optical axis of the prism for deflecting the rays emitting from the prism to the left and right eyepieces.

4. An ophthalmoscope as defined in claim 1, wherein illumination means are provided in the housing between the prism and the objective lens adjacent the path of the rays passing from the objective lens to the prism and means are provided for directing beams emitting from the illumination means towards the objective lens at a small acute angle to the optical axis.

5. An ophthalmoscope as defined in claim 1, wherein the binocular means includes a pair of objective lenses at the exit side of the prism passing the rays through the left and right eyepieces respectively intermediately through separate Porro prisms and ocular lens for providing an enlarged image and upright image impression to the observer.

6. An ophthalmoscope as defined in claim 1, wherein the binocular means is releasably attached to the housing.

7. An ophthalmoscope as defined in claim 1, wherein the housing is mounted to a support stand in a universal direction manner.

8. An ophthalmoscope as defined in claim 1, wherein a field lens is provided between the object lens and the prism.

9. An ophthalmoscope as defined in claim 1, wherein the means for directing the illumination beams towards the object lens includes a pellicle semi-transparent mirror crossing the optical axis.

* * * * *